US011085588B2

(12) United States Patent
Nikolic et al.

(10) Patent No.: US 11,085,588 B2
(45) Date of Patent: Aug. 10, 2021

(54) CASSETTE WITH A SENSOR FOR DETERMINING THE DIFFERENCE BETWEEN A FIRST AND A SECOND FLUID STREAM

(71) Applicant: FRESENIUS MEDICAL CARE DEUTSCHLAND GMBH, Bad Homburg (DE)

(72) Inventors: Dejan Nikolic, Frankfurt (DE); Alexander Heide, Eppstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 149 days.

(21) Appl. No.: 16/017,236

(22) Filed: Jun. 25, 2018

(65) Prior Publication Data
US 2018/0313499 A1  Nov. 1, 2018

Related U.S. Application Data

(60) Continuation of application No. 15/186,672, filed on Jun. 20, 2016, now Pat. No. 10,260,682, which is a
(Continued)

(30) Foreign Application Priority Data

Mar. 15, 2010 (DE) .......................... 102010002871.1
Apr. 1, 2010 (DE) .......................... 102010003642.0

(51) Int. Cl.
*A61M 1/14* (2006.01)
*A61M 1/16* (2006.01)
(Continued)

(52) U.S. Cl.
CPC ................. *F17D 1/00* (2013.01); *A61M 1/14* (2013.01); *A61M 1/16* (2013.01); *A61M 1/1605* (2014.02);
(Continued)

(58) Field of Classification Search
CPC ... F17D 1/00; A61M 1/1605; A61M 2205/12; A61M 2205/3331; A61M 2205/3334;
(Continued)

(56) References Cited

U.S. PATENT DOCUMENTS 3,522,527 A    8/1970  Williams et al.
3,946,731 A *  3/1976  Lichtenstein ........... A61M 1/16
                                                     604/66
(Continued)

FOREIGN PATENT DOCUMENTS

DE       1951378       4/1971
DE      10313685      10/2003
(Continued)

*Primary Examiner* — Brian J. Sines
(74) *Attorney, Agent, or Firm* — Jacobson Holman PLLC

(57) ABSTRACT

The invention relates to the balancing of fluid streams in a dialysis system. In particular the invention relates to a cassette for conveying a first and a second fluid stream in a dialysis system, wherein the first and the second fluid streams can be medical fluid streams such as for example dialysate streams or blood streams, wherein the cassette has a sensor as a device for balancing the first and the second fluid stream, and wherein the sensor has a first channel for the first fluid stream and a second channel for the second fluid stream. The invention further relates to a dialysis system, which is configured to accommodate at least one cassette which is configured as described above. Furthermore, the present invention relates to an arrangement by which two channels for the first and the second fluid streams
(Continued)

are formed. In addition, the invention relates to a method for construction of the two channels or the arrangement.

18 Claims, 8 Drawing Sheets

Related U.S. Application Data division of application No. 13/634,656, filed as application No. PCT/EP2011/053907 on Mar. 15, 2011, now Pat. No. 9,399,089.

(51) Int. Cl.
| | |
|---|---|
| *A61M 1/30* | (2006.01) |
| *F17D 1/00* | (2006.01) |
| *A61M 1/34* | (2006.01) |
| *G01F 1/58* | (2006.01) |
| *A61M 1/36* | (2006.01) |

(52) U.S. Cl.
CPC ............ *A61M 1/1647* (2014.02); *A61M 1/34* (2013.01); *A61M 1/341* (2014.02); *A61M 1/3403* (2014.02); *A61M 1/36* (2013.01); *A61M 1/3607* (2014.02); *G01F 1/58* (2013.01); *A61M 2205/057* (2013.01); *A61M 2205/12* (2013.01); *A61M 2205/3317* (2013.01); *A61M 2205/3331* (2013.01); *A61M 2205/3334* (2013.01); *A61M 2205/3379* (2013.01); *A61M 2207/00* (2013.01)

(58) Field of Classification Search
CPC .. A61M 1/1647; A61M 1/3403; A61M 1/341; A61M 1/14; A61M 1/16; A61M 1/34; A61M 1/36; A61M 2205/3379; A61M 2207/00; A61M 1/1601; A61M 1/30; G01F 1/58
See application file for complete search history.

(56) References Cited

U.S. PATENT DOCUMENTS

| | | | |
|---|---|---|---|
| 4,211,987 A | 7/1980 | Pan | |
| 5,417,119 A | 5/1995 | Smoll | |
| 5,702,597 A * | 12/1997 | Chevallet | A61M 1/1656 |
| | | | 210/195.2 |
| 6,452,371 B1 | 9/2002 | Brugger | |
| 6,595,943 B1 * | 7/2003 | Burbank | A61M 1/1639 |
| | | | 604/5.01 |
| 6,994,781 B2 | 2/2006 | Cork et al. | |
| 7,465,285 B2 | 12/2008 | Hutchinson et al. | |
| 8,459,292 B2 | 6/2013 | Wilt et al. | |
| 8,491,184 B2 | 7/2013 | Kamen et al. | |
| 8,721,879 B2 | 5/2014 | van der Merwe et al. | |
| 8,870,549 B2 | 10/2014 | Tracey et al. | |
| 8,932,469 B2 | 1/2015 | Childers et al. | |
| 9,028,691 B2 | 5/2015 | Grant et al. | |
| 2002/0121471 A1 * | 9/2002 | Pedrazzi | A61M 1/342 |
| | | | 210/321.71 |
| 2003/0010825 A1 | 6/2003 | Neubert | |
| 2005/0273014 A1 | 12/2005 | Granchandani et al. | |
| 2006/0096389 A1 | 5/2006 | Hallstadius et al. | |
| 2009/0032232 A1 | 2/2009 | Murayama | |
| 2009/0101550 A1 | 4/2009 | Muller et al. | |
| 2009/0104488 A1 | 4/2009 | Gruss et al. | |

FOREIGN PATENT DOCUMENTS

| | | |
|---|---|---|
| DE | 202008012801 | 3/2010 |
| EP | 0106940 | 5/1984 |
| EP | 2169359 | 3/2010 |
| GB | 2003274 | 3/1979 |
| JP | S45396608 | 12/1970 |
| JP | S4915228 | 4/1974 |
| JP | S5244214 | 11/1977 |
| JP | S5434268 | 3/1979 |
| JP | S5979810 | 5/1984 |
| JP | H01170826 | 7/1989 |
| JP | H07336139 | 12/1995 |
| JP | H10253411 | 9/1998 |
| JP | 2006238915 | 9/2006 |
| JP | 2007255755 | 10/2007 |
| JP | 2009534622 | 9/2009 |

* cited by examiner

CASSETTE WITH A SENSOR FOR DETERMINING THE DIFFERENCE BETWEEN A FIRST AND A SECOND FLUID STREAM

The invention relates to a cassette for conveying a first and a second fluid stream, to a device for dialysis treatment, to an arrangement which has channels for the first and the second fluid stream, and to a method for the construction of the channels for the first and the second fluid stream or for the construction of the arrangement.

Various methods using equipment for blood purification or blood treatment are employed in order to remove urophanic substances and withdraw fluid in cases of chronic renal failure. In the case of hemodialysis (HD), diffusive mass transport is predominant, while convective mass transport through the membrane is used for hemofiltration (HF), Hemodiafiltration (HDF) is a combination of both of these methods. In peritoneal dialysis (PD), no extracorporeal circuit is required, and the peritoneum is used as a contact membrane.

Because of the large exchange volumes in the above-mentioned methods, and also in continuous arterio-venous HF, continuous veno-venous HF and plasma filtration (PF), there is a need for exact balancing of the fluid withdrawn on the one hand with the fluid administered on the other, and of the volume to be ultrafiltrated during the entire treatment time. The state of the art includes gravimetric and volumetric balancing systems.

Methods are also known which measure continuously the fluid streams of the fluids flowing into the dialyzer and the fluids flowing out of the dialyzer, and balance these with each other. Various implementations of flow measurement sensors are used for this purpose.

The high degree of accuracy that is required, and the associated large expense involved in the selection and/or calibration of the flow sensors used for balancing, result in high costs. Additionally, it can be advantageous both for reasons of manageability for the medical staff giving the treatment, and also for reasons of hygiene, to integrate as much as possible of the equipment for a dialysis treatment relating to the extracorporeal blood circulation and the dialysate circulation in a throwaway disposable. Because these dialysis disposables or cassettes are used only once, it is desirable to keep their production costs low.

The object of the present invention is to provide an improved balancing of medical fluid streams.

The medical fluids are preferably dialysate or blood.

This object is achieved by a cassette with a first and a second fluid stream in a dialysis system, wherein the first fluid stream can be a dialysate stream or a blood stream, and the second fluid stream can be a dialysate stream or a blood stream, wherein the cassette has a sensor as a device for determining the difference between the first and the second fluid stream, and wherein the sensor has a first channel for the first fluid stream and a second channel for the second fluid stream.

The cassette can also be used for conveying blood in a dialysis system, wherein the first and the second fluid streams through the sensor are blood. It is also conceivable that the cassette has fluid systems conveying both blood and dialysate, wherein the sensor can be part of both the blood-conveying fluid system and of the dialysate-conveying fluid system. In an alternative embodiment, the single sensor can have blood flowing through its first channel and dialysate flowing through its second channel. In another alternative embodiment, two of the sensors can be present in the blood-conveying fluid system and two in the dialysate-conveying system.

It is to be noted in general that the present invention is directed generally towards the balancing of two fluid streams, or determining the difference between two fluid streams, in particular medical fluid streams. According to some example embodiments of the present invention, these fluid streams can be dialysate streams and/or blood streams. If hereinafter a particular example embodiment is directed towards a particular fluid stream such as a dialysate stream or a blood stream by way of example, it is to be understood that a similar expedient example embodiment can also be directed towards a general (medical) fluid stream. The same applies to example embodiments which are initially directed towards (medical) fluid streams in general. The example embodiments concerned can also be directed in an expedient manner towards particular medical fluid streams such as for example dialysate and/or blood streams.

According to the present invention a cassette for a dialysis system is provided, which provides a sensor as a compact component or device for balancing two fluid streams. By means of the cassette according to the invention, an independent balancing system is made possible, which ensures a high degree of accuracy in balancing.

According to an example embodiment of the present invention the first and the second channels are disposed substantially parallel to each other; wherein the sensor is configured to expose the first and the second channel to a magnetic field for balancing or determining the difference between the first and the second fluid streams. In this, the first and the second channel can be configured such that the first fluid stream in the first channel flows in the opposite direction from the second fluid stream in the second channel, or such that the first and the second fluid streams flow in the same direction.

According to the present invention the sensor is provided in the form of a compact component or device for balancing two fluid streams, which requires only a magnetic field for this balancing. Furthermore, the conveying of both streams into a common magnetic field considerably reduces errors in balancing the two fluid streams, which could arise if two independent magnetic fields, in for example two separate flow sensors, were to deviate from each other. Additionally, the sensor as a device for balancing a first and a second fluid stream can be constructed in a compact manner, obviating the necessity for a large amount of space for accommodation of the sensor in the cassette.

According to an example embodiment of the present invention, due to the magnetic field a separation of positive and negative charge carriers occurs in the first fluid stream of the first channel and in the second fluid stream of the second channel, and the sensor is configured to measure a first voltage which is produced by the separation of positive and negative charge carriers in the first fluid stream and arises due to the flow of the first fluid stream in the first channel, and to measure a second voltage which is produced by the separation of positive and negative charge carriers in the second fluid stream and arises due to the flow of the second fluid stream in the second channel, wherein the first and the second voltages are used for balancing or determining the difference between the first and the second fluid stream.

In this manner the present invention permits a highly accurate balancing of the two fluid or dialysate streams in a single device—the sensor—using a single magnetic field on the channels through which the two fluid streams flow.

According to an example embodiment of the present invention, the sensor is configured to transmit to a device for dialysis treatment at least one signal, containing the measured first and the measured second voltage or a value derived from the first and second measured voltages. In this way, the independence of the cassette and the sensor from other units, components or devices of a dialysis system is enhanced.

According to an example embodiment of the present invention, at least one voltage metering unit for the first channel is disposed on the first channel, which is configured to measure the first voltage, and at least one voltage metering unit for the second channel is disposed on the second channel, which is configured to measure the second voltage. By this means exact determination of the voltages in the channels of the device is possible according to the present invention.

According to a further example embodiment of the present invention, the sensor has a measuring cell which contains the first and the second channel and which is exposed to the magnetic field in such a manner that the same magnetic field strength and the same transient waveform of the magnetic field acts on both channels. By this means it is ensured that the magnetic field acts equally on the two channels in the sensor. The measurement cell can thereby be surrounded by the magnetic field.

According to an example embodiment of the present invention, the first and the second channels have the same shape and size. In particular, the channels are alike with respect to their shapes, sizes and dimensions. By this means the accuracy of the balancing is enhanced.

According to an example embodiment of the present invention, the first and the second channels are formed from at least three parts which have the same shape and dimensions; in each of the at least three parts a fluid passageway is formed on at least one of two surfaces located opposite each other; and the at least three parts are assembled to form the first and the second channel by stacking or lining up the at least three parts on the sides of the at least three parts that are formed with fluid passageways, in such a manner that the first channel is formed between a first and a second part of the at least three parts, and the second channel is formed between the second and a third part of the at least three parts, wherein the first and the second channel have the same shape, are parallel to each other, and are disposed side by side or one above the other. According to an example embodiment, the at least three parts are substantially cuboid in shape. According to the present invention the at least three parts can also have other suitable shapes.

This enables an extremely exact and reproducible channel cross-section, which is of great importance due to the temperature-dependence of the channel geometry in dialysis systems. Furthermore, in this manner a similar, and even identical, implementation of the two channels is made possible, which ensures, and indeed enables, the accuracy of the balancing.

According to one implementation of the present example embodiment, the at least three parts have fastening devices, by means of which the at least three parts are fitted together. This enables rapid and cost-effective production of the arrangement comprising the three channels without compromising the accuracy of the balancing.

According to one implementation of the present example embodiment, the at least three parts are parts which are manufactured by means of an identical injection mold. This facilitates the identical or at least substantially alike implementation of the channels.

According to a further implementation of the present example embodiment, the first channel has an additional voltage metering unit for the first channel, which is configured to measure a voltage produced by the separation in the first fluid stream that arises as a result of flow of the first fluid steam; the at least one voltage metering unit for the first channel is disposed on a side of the first channel which is opposite another side of the first channel on which the other voltage metering unit for the first channel is disposed, wherein the magnetic field is oriented parallel to the first and to the other side of the first channel; the second channel has a further voltage metering unit for the second channel, which is configured to measure a voltage produced by separation in the second fluid stream that arises as a result of flow of the second fluid steam, and the at least one voltage metering unit for the second channel is disposed on a side of the second channel which is opposite another side of the second channel on which the other voltage metering unit for the second channel is disposed, wherein the magnetic field is oriented parallel to the first and to the other side of the second channel.

According to a further example embodiment of the present invention, the first and the second channels are formed by the construction of a dividing wall in a channel which comprises both the first and the second channel, such that the first and the second channels have the same form, wherein the magnetic field is oriented parallel to the dividing wall.

According to one implementation of the present example embodiment, the at least one voltage metering unit for the first channel is disposed on a side of the first channel which is opposite the dividing wall; the at least one voltage metering unit for the second channel is disposed on a side of the second channel which is opposite the dividing wall; and a common voltage metering unit is disposed on the dividing wall, and is configured to measure a voltage produced by separation in the first and in the second fluid streams that arises as a result of flow of the first and second fluid steams, wherein the at least one voltage metering unit for the first channel, the at least one voltage metering unit for the second channel, and the common voltage metering unit are disposed at substantially the same height in the first and second channels.

According to another implementation of the present example embodiment, the at least one voltage metering unit for the first channel is disposed on a side of the first channel which is opposite the dividing wall; the at least one voltage metering unit for the second channel is disposed on a side of the second channel which is opposite the dividing wall; and the at least one voltage metering unit for the first channel and the at least one voltage metering unit for the second channel are disposed at substantially the same height in the first and the second channels.

It is apparent from the two previous example embodiments that the cassette and the sensor as a device for balancing can be implemented according to the present invention in a manner which is highly variable and adaptable to particular requirements, without forfeiting the advantages mentioned above and hereinafter.

The object of the present invention stated above is also achieved by means of a device for dialysis treatment, wherein the device for dialysis treatment has at least one accommodation means, which is configured to accommodate at least one cassette which corresponds to the cassette mentioned above and hereinafter described in more detail.

According to an example embodiment, the device for dialysis treatment is configured to capture a first voltage and a second voltage, wherein the first voltage corresponds to the first fluid stream and the second voltage corresponds to the first fluid stream, and wherein both the first and the second voltage were measured by the cassette's sensor which is outlined above and explained in greater detail hereinafter.

According to an example embodiment of the present invention, the device for dialysis treatment has a control unit, which is configured to control and/or to regulate the flow of a medical fluid using the signal. The control unit is configured to control the delivery rates of at least one pump. According to an example embodiment of the present invention, the pump comprises one of the following pumps: a blood pump; a dialysate pump; an ultrafiltration pump.

The object of the present invention stated above is also achieved by means of an arrangement which has at least three parts with the same shape and dimensions, wherein in each of the at least three parts a fluid passageway is formed on at least one of two surfaces located opposite each other, and wherein the at least three parts are assembled to form a first and a second channel by stacking or lining up the at least three parts on the sides of the at least three parts that are formed with fluid passageways, in such a manner that the first channel is formed between a first and a second part of the at least three parts, and the second channel is formed between the second and a third part of the at least three parts, wherein the first and the second channel have the same shape, are parallel to each other, and are disposed side by side or one above the other. According to an example embodiment, the at least three parts are substantially cuboid in shape. According to the present invention the at least three parts can also have other suitable shapes.

According to an example embodiment, the arrangement is configured for insertion in a device for balancing a first and a second fluid stream, wherein the first and the second fluid streams are, or can be, dialysate streams or blood streams, and wherein the first channel is configured for a first fluid stream and the second channel is configured for a second fluid stream.

According to an example embodiment of the present invention, the above-mentioned device for balancing a first and a second fluid stream corresponds to the cassette's sensor which is outlined above and explained in greater detail hereinafter.

According to an example embodiment of the present invention, the at least three parts have fastening devices, by means of which the at least three parts are fitted together.

According to a further example embodiment of the present invention, the at least three parts are parts which are manufactured by means of an identical injection mold.

The object of the present invention stated above is furthermore also achieved by means of a method for the construction of a first channel for a first fluid stream and for the construction of a second channel for a second fluid stream, wherein the first and the second fluid streams are, or can be, dialysate streams or blood streams, wherein the first and the second channels are constructed by means of at least three parts which have the same shape and dimensions, wherein in each of the at least three parts a fluid passageway is formed on at least one of two surfaces located opposite each other, and wherein the method comprises:

Assembly of the at least three parts for forming the first and the second channels by stacking or lining up the at least three parts on the sides of the at least three parts that are formed with fluid passageways, in such a manner that the first channel is formed between a first and a second part of the at least three parts, and the second channel is formed between the second and a third part of the at least three parts, wherein the first and the second channel have the same shape, are parallel to each other, and are disposed side by side or one above the other.

According to an example embodiment of the present invention, the at least three parts are substantially cuboid in shape. According to the present invention the at least three parts can also have other suitable shapes.

According to an example embodiment of the present invention, the three parts have fastening devices and their assembly comprises a fitting together of the three parts by means of the fastening devices.

The at least three parts can be attached to each other in a fluid-tight manner using various technical means, e.g. using transmission laser welding, mirror welding, ultrasonic welding, bonding etc.

The subject-matters of the present invention, which were briefly introduced above and will be explained in greater detail hereinafter, enable an independent balancing of dialysate flows which is significantly improved with respect to its accuracy. The present invention additionally permits a cost-effective solution to the balancing of dialysate flows, which fulfils at the same time the exacting requirements for accuracy of measurement and for precision of implementation and design.

Example embodiments of the present invention will be described in detail below with reference to the appended drawings.

BRIEF DESCRIPTION OF THE DRAWINGS

The drawings show:

FIG. 1a and FIG. 1b show the use of a cassette 10 to convey dialysis streams 105, 106 in a dialysis device according to one example embodiment of the present invention in each case. It is to be noted with respect to FIGS. 1a and 1b that the units, components or devices that have the same reference signs in both FIG. 1a and FIG. 1b correspond to the same units, components or devices in both example embodiments. The dialysis device is not shown in FIG. 1a and FIG. 1b, but can be implemented for example as suggested in FIG. 7. The dialysis device has an accommodation means which can accommodate the cassette 10. The cassette 10 has, according to the present example embodiments, two centering units 107, by means of which the cassette 10 can be inserted in the dialysis device and located in the desired position. The centering units 107 can be implemented for example as guide holes for pins protruding from the dialysis device. The present invention also permits the use of other means for inserting the cassette 10 in the dialysis device, and is not restricted to the centering units 107.

Figure 1A:
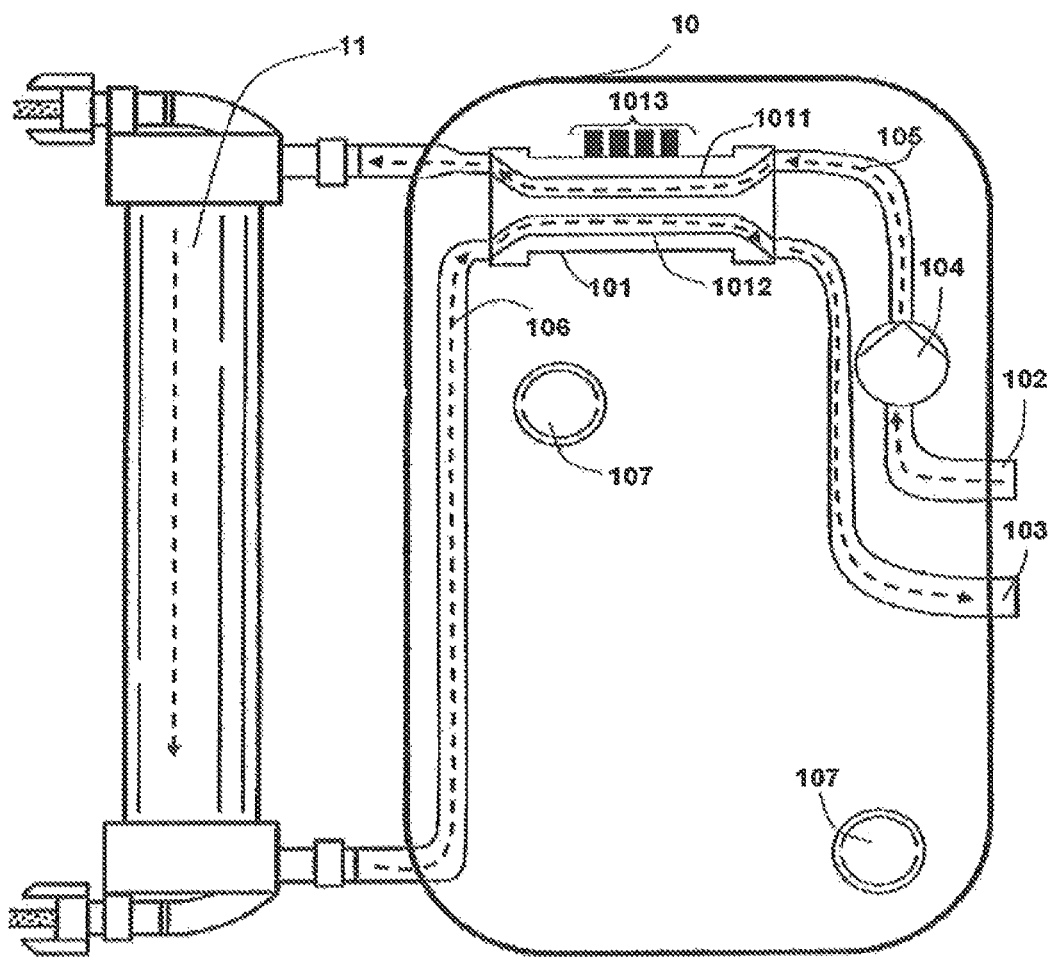
FIG. 1a the use of a cassette for conveying dialysate streams in a dialysis device according to an example embodiment of the present invention.
Figure 1B:
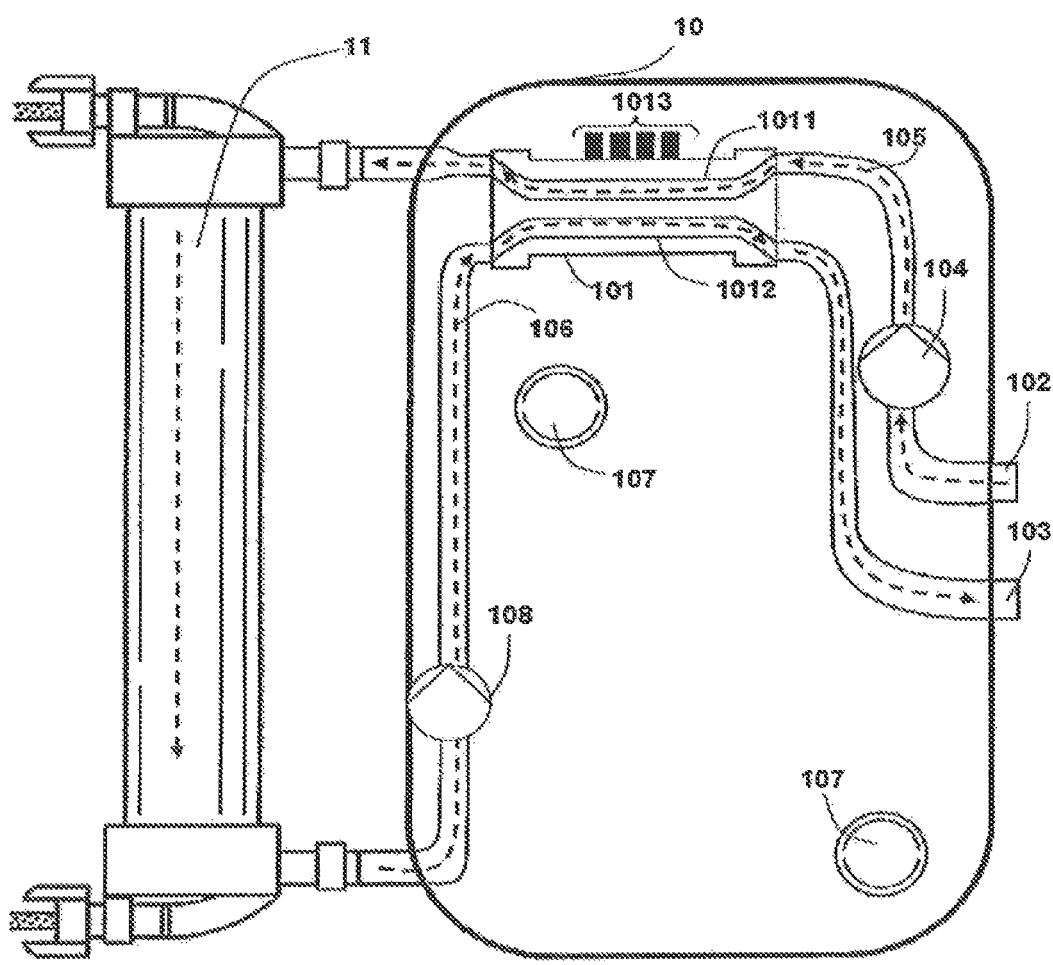
FIG. 1b the use of a cassette for conveying dialysate streams in a dialysis device according to a further example embodiment of the present invention.

Cassettes such as cassette 10 for conveying dialysate streams are generally known. A conventional cassette is described in the patent application DE 102 24 750, for example. The representations of cassette 10 that are shown in FIG. 1a and FIG. 1b focus substantially on those parts of the cassette according to the invention that are essential for the present example embodiment. Thus other devices, units or components of a dialysis circulation (e.g., sensors, actuators etc.) which can typically be located in the cassette 10 are not shown in FIG. 1a and FIG. 1b for reasons of clarity, but can be incorporated in cassette 10 according to the present example embodiment.

Cassette 10 has, as shown in FIGS. 1a and 1b, a dialysate inlet 102 from a source of fresh dialysate and a dialysate outlet 103.

In order to pump the dialysate stream 105, the cassette 10 according to the present example embodiment has a dialysate pump 104. The pumping rate of the dialysate pump 104 determines the magnitude of the dialysate flow rate.

According to the example embodiment of FIG. 1b the cassette 10 can additionally have an ultrafiltration pump 108, which can remove dialysate from the dialysis filter 11 downstream from the dialysis filter.

The dialysate stream 105 flows from the source of fresh dialysate into the inlet 102 via the sensor 101, which is configured for balancing fluid streams, to the dialysis filter 11. In the dialysis filter 11 a mass transfer takes place via the semipermeable membrane of the dialysis filter 11 between the patient's blood and the dialysate, as a result of which the patients blood is cleansed of toxins. In addition, fluid can be filtered from the blood into the dialysate via the membrane by means of a pressure difference between the dialysate side and the blood side of the semipermeable membrane, in order to remove water from the patient's blood. The volume of fluid that is filtered from the patient's blood onto the dialysis side per unit of time is known as the ultrafiltration rate, and is prescribed for each individual case by the physician in charge of the treatment. Because of the transfer of fluid in the dialysis filter 11, the dialysate stream 106 which flows out of the dialysis filter 11 is greater than the dialysate stream 105 which flows into the dialysis filter 11. Because the difference between the two streams 105, 106 can only originate from the patient's blood, this difference is equal to the ultrafiltration rate.

The ultrafiltration rate depends, alongside the characteristics of the dialysis filter 11, primarily on the pressure difference between the blood side and the dialysis side of the dialysis filter 11. The higher the excess pressure on the blood side, the more fluid is filtered from the blood onto the dialysate side. The pressure to be set on each side of the semipermeable membrane is proportional to the supply side of the blood and the dialysate. Thus the ultrafiltration rate can be regulated by the control or regulation of the pumping rate of, preferably, the dialysate via the dialysate pump 104.

Control of the blood pump (not shown in FIGS. 1a and 1b), or of both the blood and the dialysate pumps, is also conceivable.

Because the blood flow and/or dialysate flow is prescribed for treatment purposes by the physician, and these volumes are therefore variable only to a small extent, the transmembrane pressure can also be produced using the ultrafiltration pump 108 (see FIG. 1b). This draws additional dialysate 106 from the dialysate filter 11 downstream of the dialysate filter. This can take place continually or periodically. If the dialysate is pumped by occlusion upstream from the dialyzer, for example by the implementation of the dialysate pump 104 as a peristaltic roller pump, the additional volume removed by the ultrafiltration pump 108 from the dialysis filter 11 via the semipermeable membrane of the dialysis filter 11 must originate from the blood and thus represents the ultrafiltrate. In this case the ultrafiltration can take place continuously. If the dialysate is not pumped upstream from the dialyzer by occlusion, for example by the implementation of the dialysate pump 104 as a centrifugal pump, additional occlusion means must be provided upstream of the filter 11 (e.g. squeeze valves, not shown in FIG. 1b), which occlude the dialysate fluid system during the pumping of the ultrafiltration pump 108. In this case the additional volume removed by the ultrafiltration pump 108 via the semipermeable membrane of the dialysis filter 11 must originate from the blood and thus represents the ultrafiltrate. In this case the ultrafiltration takes place periodically. The dialysis pump 104 and the ultrafiltration pump 108 then operate alternately.

In both cases the additional fluid volume, which represents the ultrafiltrate, flows via the sensor 101 and the channel 1012. The ultrafiltration volume is thereby known. The sensor signals from the sensor 101 can then also be used in this embodiment, in a manner described in more detail below, to adjust the delivery rate of the ultrafiltration pump 108 so that the desired ultrafiltration rate is achieved.

The sensor 101 has a first channel 1011 for the passage of the blood or dialysis stream 105 coming from the patient, and a second channel 1012 for the passage of the blood or dialysis stream 106 flowing to the patient after filtering. The designations "first" and "second" in this description are not to be regarded as restrictive, and serve only to facilitate the distinguishing between the two channels 1011, 1012 in sensor 101.

The two channels 1011, 1012 are disposed substantially parallel to each other. They can be arranged one above the other or side by side: the present invention imposes no restriction in this respect. The blood or dialysate streams 105, 106 flow in the sensor 101 according to the present example embodiment in opposite directions from each other. The present invention is, however, not limited to the streams 105, 106 flowing in opposite directions. According to another example embodiment the fluid streams 105, 106 can also flow in the same direction.

A further example embodiment, analogous to the example embodiment in FIG. 1, is realized by the use of the sensor 101 for balancing blood. Because fluid is filtered from the blood side to the dialysate side during the ultrafiltration, the possibility also exists of balancing on the blood side, since the blood streams in and out of the dialysis filter are thereby different. This difference can also be detected by sensor 101. This example embodiment can be configured analogously to the example embodiment in FIG. 1, with the difference that the blood at inlet 102 now flows via the first channel 1011 of sensor 101. From there the blood is conveyed, via the lower blood inlet of the dialysis filter, through the filter, and from the upper blood outlet of the filter through the second channel 1012 of the sensor. It is in principle also possible to integrate both embodiments in one cassette 10, which then has two sensors 101.

According to the present example embodiment in FIG. 1, the sensor 101 captures the voltages that arise due to the flow of the blood stream or dialysis stream 105 in channel 1011 and due to the flow of the blood stream or dialysis stream 106 in channel 1012. The capturing of the voltages will be explained more precisely with reference to the example embodiment in FIG. 2. The voltages are captured in sensor 101 by means of appropriate voltage metering units, which can be for example electrodes. The use of voltage metering units in this context is generally known, and will therefore not be explained in detail; see for example the patent application GB 2 003 274 A, in which the use if electrodes is disclosed. According to the present invention, any suitable known voltage metering units can be used.

The sensor 101 is configured to transmit or send the captured or measured voltages from the blood or dialysate streams 105, 106 in the channels 1011, 1012 to the dialysis device. According to the present example embodiment the sensor 101 has four voltage metering units, which are not shown in FIG. 1, with two of the units disposed on each of the channels 1011, 1012. According to the present invention the number of voltage metering units that are used can vary, and is not restricted to the use of four voltage metering units. According to the present example embodiment electrodes are used as voltage metering units. In order to pass or transmit the measured voltages to the dialysis device, the sensor 101 has at least one transmission unit. According to the present example embodiment this transmission unit is a contact. Furthermore, according to the present example embodiment four transmission units 1013 in the form of contacts are employed. According to the present invention the number of transmission units 1013 that are employed can vary, and is not restricted to the use of four transmission units 1013. According to the present example embodiment the number of transmission units 1013 corresponds to the number of voltage metering units. Thus each electrode that is used as a voltage metering unit is allocated to one transmission unit, or one contact 1013. The contacts 1013 are the contacts of the four electrodes. According to the present example embodiment the contacts 1013 are led out of the sensor 101 on one side of the sensor 101 and connected conductively with the dialysis device. By means of these contacts 1013 the sensor 101 transmits the voltage values that are determined or captured to the dialysis device, which can read off the voltage values from the contacts 1013.

The voltage values of channels 1011, 1012 are used for balancing the blood or dialysis streams 105, 106. This will be explained in more detail with reference to FIG. 8.

It is to be noted that the present invention is not restricted to the use of contacts 1013 as transmission units 1013. Thus for example an inductor, embodied as a receiver coil, can produce energy in the cassette by induction from an alternating magnetic field, which is supplied by the dialysis machine or device, and, in a known manner via rectification of the alternating voltage arising in the receiver coil, provide an electronic voltage integrated in the cassette. This electronic circuit can be configured so as to process the voltage values from the voltage metering units of sensor 101, and from these generate a signal which is transmitted to the dialysis machine or device in a contactless manner, e.g. by radio or via load modulation of the receiver coil.

Figure 2:
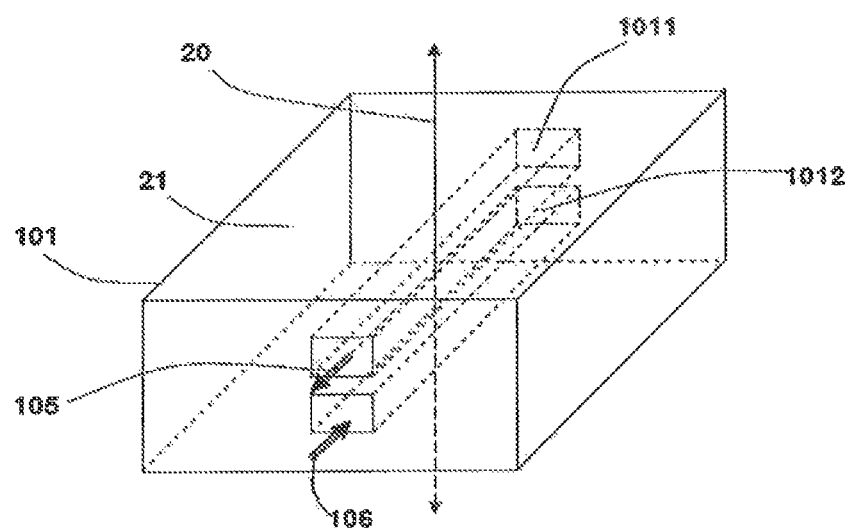
FIG. 2 a device for balancing a first and a second fluid stream according to an example embodiment of the present invention.

FIG. 2 shows a device 101 for balancing a first and a second fluid stream according to an example embodiment of the present invention. The device 101 according to the present example embodiment corresponds to the sensor 101 shown in FIG. 1, and shows a detailed implementation of the sensor 101.

According to the present example embodiment the sensor 101 has a measuring cell 21, which is disposed in the interior of the sensor 101. The measuring cell 21 encompasses or is directed towards channel 1011 and channel 1012. According to the present example embodiment the channels 1011, 1012 are shown by way of example as cuboids. It is however to be noted that the present invention is not restricted to cuboid channels; the present invention is also applicable to other shapes which can be used for channels, e.g. to cylindrical channels etc. The two channels 1011, 1012 are alike or identical with regard to their forms. In particular, they are implemented alike or identically with regard to their shape, size and dimensions.

According to the present example embodiment the measuring cell 21 of the sensor 101 is constructed or disposed such that the two streams 105, 106 in two separate channels 1011, 1012 flow past in opposite directions from each other. If the measuring cell 21 in the sensor 101 is brought into a magnetic field which is oriented perpendicular to the direction of flow of the blood or dialysate streams 105, 106 or to the channels 1011, 1012, a charge separation of the positive and negative charge carriers occurs in the fluid. The driving force in this is the Lorentz force. The perpendicular orientation of the magnetic field relative to the blood or dialysate streams 105, 106 or to the channels 1011, 1012 is made clear in FIG. 2 by means of the arrow 20. For balancing the blood and dialysate streams 105, 106, the voltages generated in the channels 1011, 1012 by the charges that arise are measured.

In this the potential difference depends on the distance and/or on the strength of the magnetic field. According to the present example embodiment the conductivity of the medium in the sensor 101 does not play a decisive role. However, according to the present example embodiment a minimum conductivity should be present. For this the following formula applies:

$$U = B*v*D, \quad (1)$$

where U is the voltage, B the field strength, v the flow velocity and D the internal diameter of the channel 1011, 1012.

Both the blood or dialysate flowing in the channel 1011 and the blood or dialysate flowing in the channel 1012 produce a voltage. If the blood or dialysate from channel 1011, after leaving the measuring cell 21, were to flow back directly into the inlet of channel 1012, the induced voltages would exactly cancel each other out. In other words the difference in voltage between the first channel 1011 and the second channel 1012 would equal zero. If a calculation of the difference between the two voltages results in a value not equal to zero, the volumetric flow rates in the two channels 1011, 1012 must be unequal. This is normally the case in dialysis devices, since after leaving the measuring cell 21 the blood or dialysate stream 105 from the channel 1011 does not flow back directly into the inlet of channel 1012 as blood or dialysate stream 106, but first makes its way to the filter 11, where changes occur to the fluid streams as a result of the ultrafiltration. In the field of dialysis systems, a rate derived from differences in the voltages of channels 1011, 1012 is designated the ultrafiltration rate.

According to formula (1), with identical internal diameters D1=D2=D of the two measurement channels 1011 and 1012 and an identical field strength B, then the field B1=B2=B in both measurement channels 1011, 1012. See formula (2):

$$U1-U2=v1-v2, \quad (2)$$

where v1–v2 is the differential flow between the two channels 1011, 1012, and according to the present embodiments this differential flow is identical with the ultrafiltration rate.

In order to determine the ultrafiltration rate it is thus unnecessary, according to formula (2), to know the exact dimensions of the measurement channels 1011, 1012 or the strength of the magnetic field. Only if an absolute measurement of the flow rates through the two channels is desired is it necessary to know D and B.

Figure 3A:
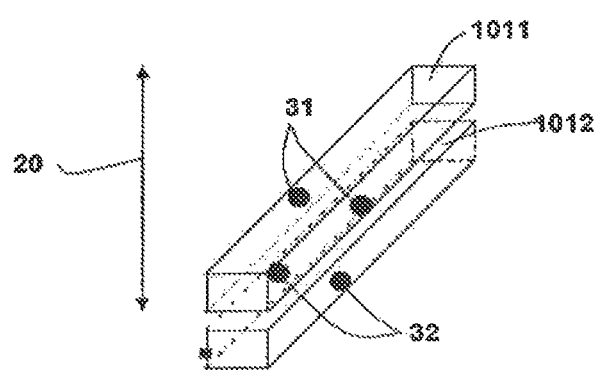
FIG. 3a, 3b channels for the first and the second fluid stream disposed in a device for balancing a first and a second fluid stream according to an example embodiment of the present invention.
Figure 3B:
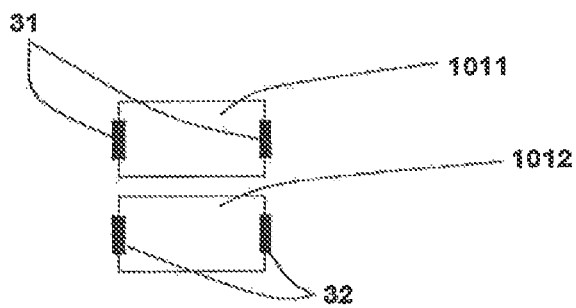

FIGS. 3a and 3b show a detailed view of the channels 1011, 1012 according to an example embodiment of the present invention. According to the present example embodiment both the first channel 1011 and the second channel 1012 have voltage metering units for measuring the voltages in the channels 1011, 1012, which are produced as described above by the separation of charges and arise due to the flow of each of the fluid streams 105, 106. According to the present example embodiment the voltage metering units 31, 32 are electrodes. In this case each channel 1011, 1012 has an electrode 31, 32 on each of two opposite sides of the channel 1011, 1012. According to the present example embodiment the electrodes 31, 32 are disposed parallel to the orientation 20 of the magnetic field.

It is to be noted that the present invention is not restricted to the use of two electrodes as voltage metering units per channel 1011, 1012. FIGS. 3a and 3b show merely an embodiment of the present invention by way of example.

Because according to the present example embodiment two voltage values are provided for the channels 1011 and 1012, according to formula (2) the difference between the two measured voltage values is determined in order to balance the blood or dialysis streams 105, 106. The excitatory magnetic field B can be either an unchanging magnetic field or an alternating magnetic field. The voltages which arise are direct voltages in the case of an unchanging excitatory magnetic field, and alternating voltages in the case of an alternating excitatory magnetic field. In both cases the momentary amplitude of the voltage that arises is modulated by the momentary fluid flow. The calculation of the difference between the two voltage values takes place in a manner known to the skilled person, e.g. via an analog subtractor circuit or by digitalization of the measured values and subsequent mathematical operations in a calculating apparatus provided for the purpose, which can be part of a control apparatus of the dialysis machine or dialysis device.

Figure 4A:
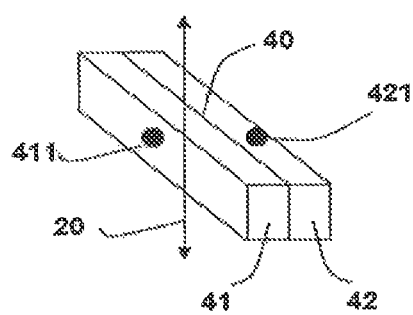
FIG. 4a, 4b channels for the first and the second fluid stream disposed in a device for balancing a first and a second fluid stream according to two further example embodiments of the present invention.
Figure 4B:
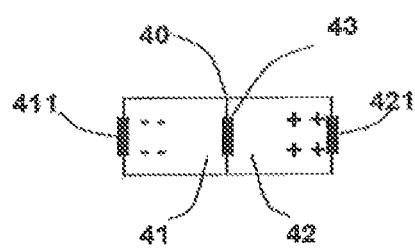

FIG. 4a, 4b show channels 41, 42 for a first and a second fluid, blood or dialysis stream disposed in a device for balancing a first and a second fluid stream according to two further example embodiments of the present invention.

According to the example embodiment in FIG. 4a, the two channels 41, 42 are separated by a dividing wall 40. In this the dividing wall 40 is disposed in a channel which was originally larger such that the channels 41, 42 are alike, with the channels 41, 42 in particular alike with respect to their shape, size and dimensions. According to the present example embodiment each of the channels 41, 42 has a voltage metering unit 411, 421. According to the present example embodiment the voltage metering units 411, 421 are electrodes, and are disposed on exterior walls of the channels 41, 42 which are opposite each other, wherein the exterior walls are the exterior walls which are disposed parallel to the orientation 20 of the magnetic field. According to the present example embodiment each electrode 411, 421 directly supplies the voltage value of the corresponding channel 41, 42.

According to the example embodiment in FIG. 4b, the two channels 41, 42 are also separated by a dividing wall 40, which is disposed as explained with reference to FIG. 4a. According to the example embodiment in FIG. 4b, the two channels 41, 42 have a total of three voltage metering units 411, 421, 43 in the form of electrodes. The example embodiment in FIG. 4b represents an extension of the example embodiment in FIG. 4a, in which a common voltage metering unit 43 in the form of an electrode for measuring the voltage in both channels 41, 42 is disposed in the dividing wall 43 between the electrodes 411, 421 at the same height as the electrodes 411, 421. In a manner similar to the example embodiments in FIG. 3a and FIG. 3b respectively, further calculations are here required, based on the voltage values in the channels 41, 42 as determined by the electrodes 411, 421, 43, in order to determine the voltage value of each channel 41, 42. As explained with respect to FIG. 3a and FIG. 3b, the skilled person is familiar with such calculations (e.g. using amplitudes or average values), and they will therefore not be described in detail. According to the present invention any commonly used calculation method that is suitable for the current situation can be chosen and employed. According to the present example embodiment the signal is applied symmetrically around the potential of the common middle electrode. For this only an additional electronic evaluation unit (familiar to the skilled person) is required.

Figures 5A, 5B, 5C:
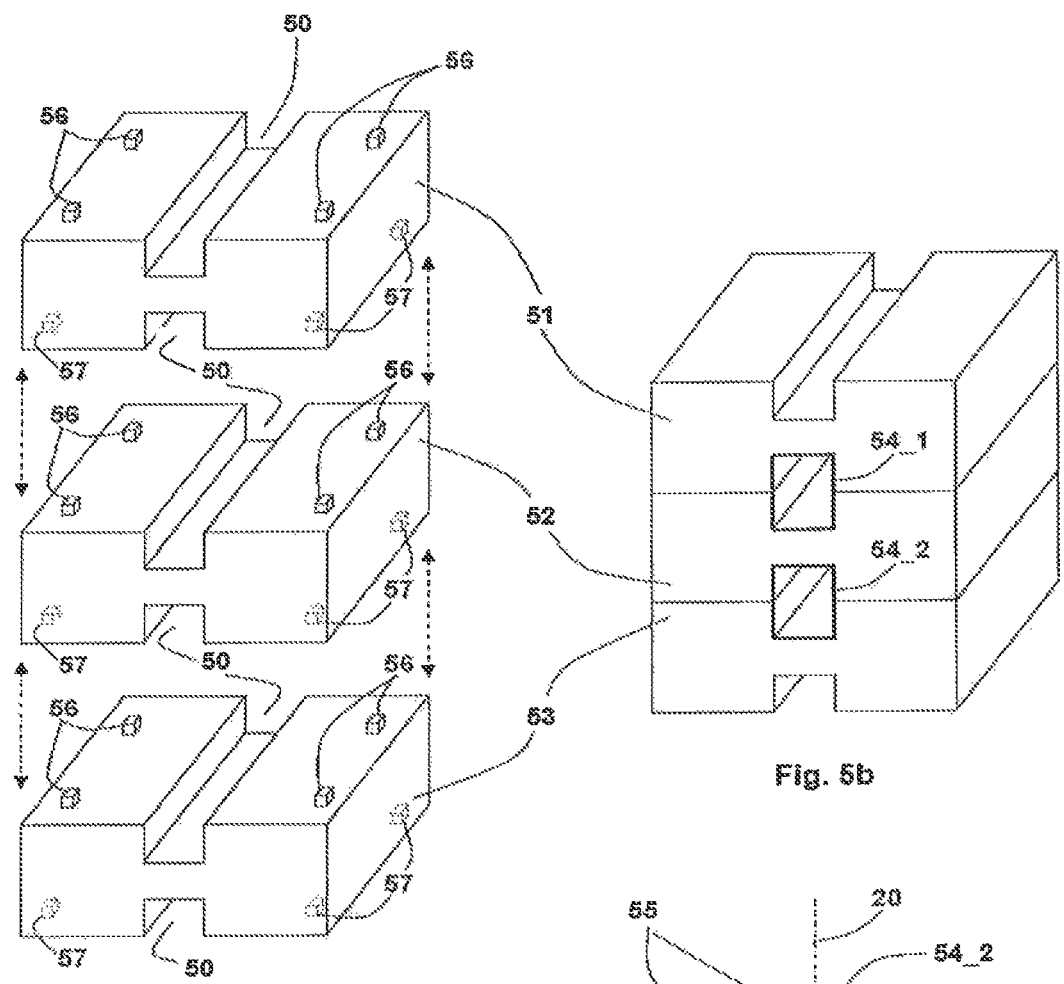
FIG. 5a, 5b, 5c an arrangement which has two channels for two fluid streams, and the construction of the arrangement according to an example embodiment of the present invention.

FIG. 5a and FIG. 5b show an arrangement which has two channels 54_1, 54_2 for two fluid, blood or dialysate streams, and the construction of this arrangement according to an example embodiment of the present invention.

Due to the temperature-dependence of the geometry of the channels, it is necessary to have an exceptionally exact and reproducible channel cross-section. This requirement is inconsistent with the requirement for an economically-priced disposable article. The cassettes (see cassette 10 in FIG. 1) that are used in dialysis devices to convey blood or dialysis streams are disposable articles. Because of the disposable character of the cassettes, their manufacture must be designed to be as inexpensive as possible. According to the present example embodiment the measuring cell 21 is preferably manufactured from symmetrical parts 51, 52, 53. According to the present example embodiment the parts 51, 52, 53 are manufactured from the same injection mold or from a single mold. The three parts 51, 52, 53 are alike with respect to their shape and dimensions. According to the present example embodiment the parts 51, 52, 53 are substantially cuboid in shape. Each of the parts 51, 52, 53 additionally has a fluid passageway 50 on two opposite sides. According to the present example embodiment the three parts 51, 52, 53 are joined together by stacking the sides which are provided with fluid passageways 50 on top of each other. According to the present example embodiment each of the parts 51, 52, 53 has nubs 56 on one of the sides to be joined, and recesses 57 on the other side to be joined which fit the nubs 56, so that when the parts 51, 52, 53 are stacked on top of each other they are fitted together with each other by means of the nubs 56 and the corresponding recesses 57 as fastening devices. According to the present example embodiment the nubs 56 and the recesses 57 are shown by way of example substantially cuboid in shape. It is to be noted concerning this that the present invention is not restricted to the cuboid shape shown for the nubs 56 and the recesses 57, and that it also permits other suitable forms of the nubs 56 and the recesses 57. Furthermore, according to the present invention other suitable fastening devices can also be employed. FIG. 5*b* shows the completed arrangement constructed from the parts 51, 52, 53, which has two identical channels 54_1, 54_2 which are parallel to each other and disposed one above the other.

As each part 51, 52, 53 can have a typical mechanical fault, it is necessary to combine or arrange the channels skillfully to join together in each case an upper half-channel from the upper parts 51, 52 and a lower half-channel from the corresponding lower parts 52, 53 into a whole channel 54_1, 54_2. Small recesses and/or protuberances can ensure the appropriate positioning. Even if the positioning of the parts 51, 52, 53 is not exact, i.e. if the corresponding upper and lower halves of the channels are not exactly located one above the other, the two whole channels 54_1, 54_2 are identical.

In this manner great accuracy can be achieved in the measuring cell 21 by very simple means.

According to the present example embodiment the fluid passageways 50 have a substantially cuboid shape, which also leads to a cuboid implementation of the whole channels 54_1, 54_2. It is to be noted that this form of the fluid passageways 50 and the channels 54_1, 54_2 is shown by way of example, and that according to the present invention additional suitable forms are also possible for the fluid passageways 50 and consequently for the channels 54_1, 54_2, FIG. 6*a* and FIG. 6*b* show an arrangement which has two channels for two fluid, blood or dialysate streams, and the construction of this arrangement according to a further example embodiment of the present invention.

Figures 6A, 6B:
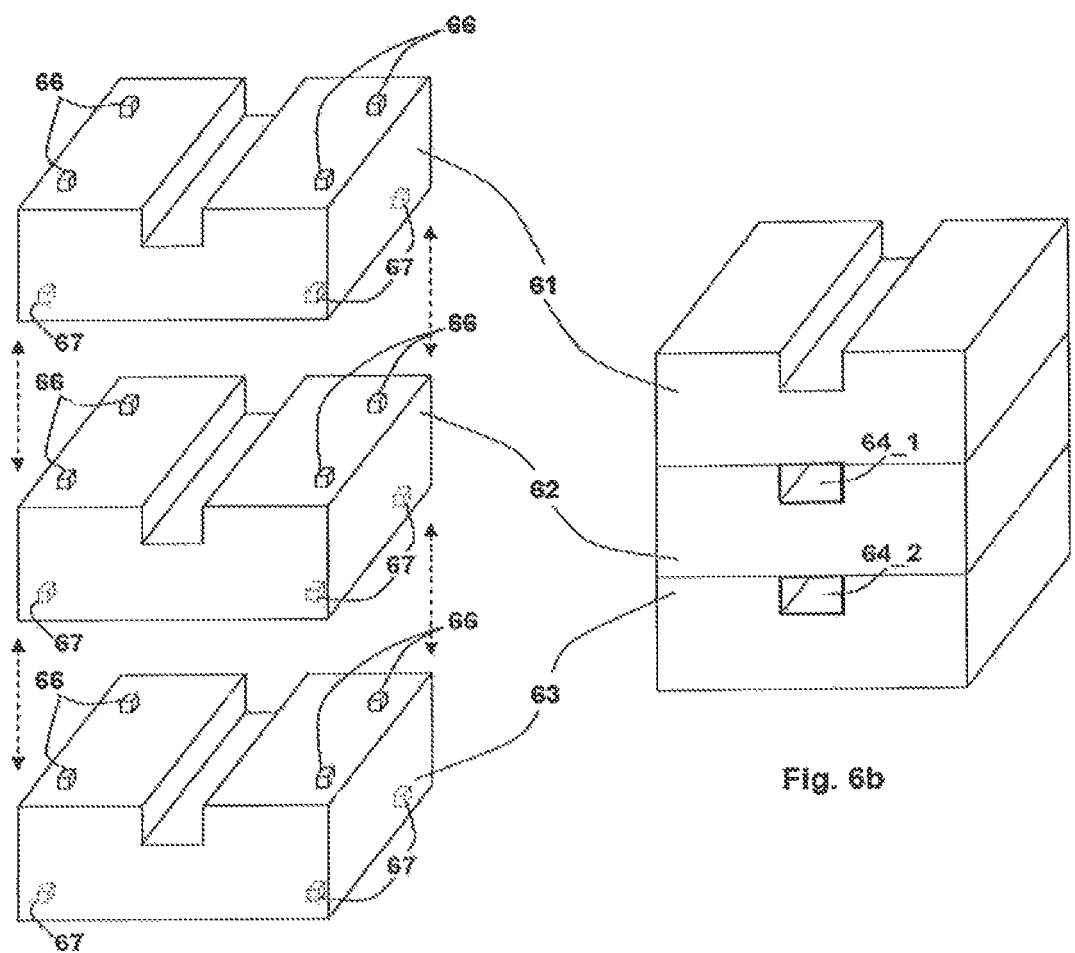
FIG. 6a, 6b an arrangement which has two channels for two fluid streams, and the construction of the arrangement according to a further example embodiment of the present invention.

The example embodiment in FIG. 6*a* and FIG. 6*b* corresponds to the example embodiment in FIG. 5*a* and FIG. 5*b*. The difference between the two example embodiments is that according to FIG. 6*a* and FIG. 6*b* the parts 61, 62, 63 each have a fluid passageway 60 on only one side. The assembly of the arrangement according to FIG. 6*a* and FIG. 6*b* from the parts 61, 62, 63 takes place similarly to the assembly of the parts 51, 52, 53 in FIG. 5*a* and FIG. 5*b*. According to the present example embodiment one side of a part 62, 63 which is formed with a fluid passageways 60 is assembled together with one side of a part 61, 62 which is not formed with a fluid passageways 60. In this it must be ensured that the identical parts 61, 62, 63 are assembled such that the fluid passageways 60 are disposed parallel to each other and one above the other. FIG. 6*b* shows clearly the channels 64_1, 64_2 created by the assembly of the parts 61, 62, 63. The advantage of this example embodiment is that it does not require 100% accurate positioning of the parts 61, 62, 63, and that slight deviations are possible, since no exceptionally careful alignment is required of an upper part of the channel 54_1, 52_2 with the lower part of the channel 54_1, 52_2.

According to the present example embodiment each of the parts 61, 62, 63 has nubs 66 on one of the sides to be joined, and recesses 67 on the other side to be joined which fit the nubs 66, so that when the parts 61, 62, 63 are stacked on top of each other they are fitted together with each other by means of the nubs 66 and the corresponding recesses 67 as fastening devices. In a similar manner to the example embodiment of FIGS. 5*a* and 5*b*, the nubs 66 and the recesses 67 are shown by way of example substantially cuboid in shape in the present example embodiment. It is similarly to be noted here that the present invention is not restricted to the cuboid shape shown for the nubs 66 and the recesses 67, and that it also permits other suitable forms of the nubs 66 and the recesses 67. Furthermore, according to the present invention other suitable fastening devices can also be employed.

According to the example embodiment in FIG. 5*a* and FIG. 5*b* and according to the example embodiment in FIG. 6*a* and FIG. 6*b*, the magnetic field can be oriented 20 perpendicular to the stacked parts 51, 52, 53 and 61, 62, 63. This is shown by way of example in FIG. 5*c*. According to the example embodiment in FIG. 5*c* a DC field situation has arisen through the action of the magnetic field. The channel 54_2 shown by way of example has two electrodes 55 as voltage metering units. Here the electrode 55 disposed on the left hand side is configured to measure the voltage of the negative charge carrier, and the electrode 55 disposed on the right hand side is configured to measure the voltage of the positive charge carrier. As already mentioned, the charge separation of the positive and negative charge carriers occurs due to the action of the magnetic field perpendicular 20 to the channel 54_2 in the measuring cell 21 or in the sensor 101.

According to an example embodiment of the invention a sensor signal (which originates for example in the sensor 101) can be used as a measure of the differential flow between dialysate flowing into a dialysis device (i.e. blood or dialysate flow 105 from the patient) and dialysate flowing out of the dialysis device (i.e. blood or dialysate flow 106 to the patient), in order to regulate the flow of the dialysate pump.

Greater outflow than inflow means that fluid from the patient's blood has entered the dialysate via the semipermeable membrane in the dialysis filter. This fluid per unit of time corresponds to the ultrafiltration rate.

The ultrafiltration rate is prescribed for treatment purposes by the physician. If one now leads the sensor signal to a control or regulating unit, which regulates the pump flow (i.e. the settings of the blood pump or dialysis pump) depending on the desired value of the differential flow (the difference between the voltages in the channels of the sensor), the ultrafiltration rate can be controlled.

The ultrafiltration rate depends on the transmembrane pressure, which depends substantially on the blood or dialysate flow 105 from the patient and on the blood or dialysate flow 106 to the patient, as well as on the characteristics of the dialyzer (e.g. high-flux characteristic).

By means of the knowledge of the differential flow the pump output of either the dialysate pump or the blood pump, or both, can be adjusted so that the desired ultrafiltration rate is achieved. In this it is often preferred not to change the blood or dialysate flow 105 from the patient, in order not to stress the patient. A lower blood or dialysate flow 106 to the patient can mean a higher transmembrane pressure from the side of the flow 105 from the patient to the side of the flow 106 to the patient, as a result of which more fluid is filtered from the side of the flow 105 from the patient to the side of the flow 106 to the patient.

The reverse case represents refiltration, which however as a rule is not desired.

Figure 7:
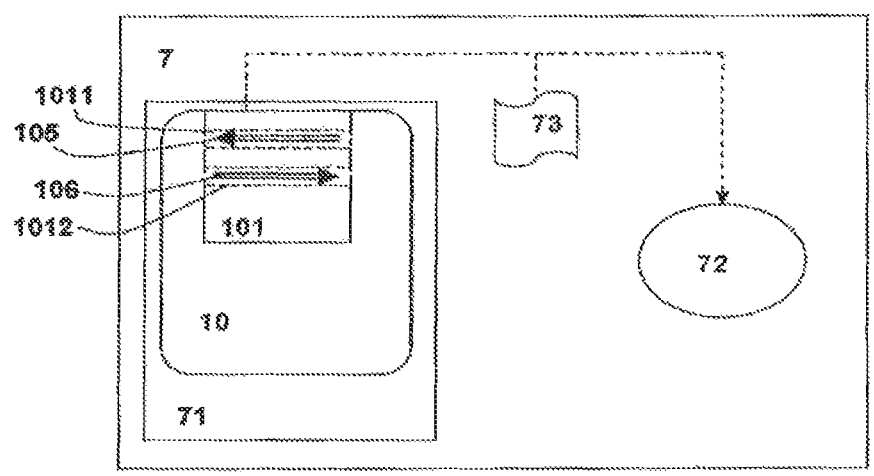
FIG. 7 a dialysis device which is configured according to an example embodiment of the present invention.

FIG. 7 shows a dialysis device 7, which is configured or implemented for dialysis treatment according to an example embodiment of the present invention. According to the present example embodiment the dialysis device 7 has an accommodation unit 71, which is configured to accommodate at least one cassette for conveying blood or dialysate streams 105, 106. According to the present example embodiment the cassette is the cassette 10 described with reference to FIG. 1. For reasons of clarity. FIG. 7 shows those parts, units and/or components of the dialysis device 7 that are essential to the present example embodiment. The dialysis device 7 has also, of course, other parts, units and/or components that are usually comprised in dialysis devices, and which enable the dialysis device 7 to function in accordance with its intended purpose. For reasons of clarity, these usual parts, units and/or components of a dialysis device are not shown in FIG. 7. As already described with reference to the example embodiment in FIG. 1, the cassette 10 comprises the sensor 101 for balancing the blood or dialysate stream 105 from the patient and the blood or dialysate stream 106 to the patient, wherein the two streams 105, 106 flow parallel to each other and, according to the present example embodiment, in opposite directions from each other in their respective channels 1011, 1012 of the sensor 101. (The streams 105, 106 can also flow in the same direction.)

According to the present example embodiment, the dialysis device 7 is configured or implemented to capture a signal which contains a difference between the voltage captured in the channel 1011 and that captured in the channel 1012. As already explained above, the respective voltages arise through a perpendicular orientation 20 of the magnetic field relative to the channels 1011, 1012 in the sensor 101 and through the flowing of the respective blood or dialysate streams 105, 106 in the channels 1011, 1012. It is however to be noted that the perpendicular orientation of the magnetic field is only an example orientation of the magnetic field, and that according to the present invention additional angles of orientation of the magnetic field may also be used.

The sensor 101 has suitable voltage metering units, which are configured to measure the respective voltages in the channels 1011, 1012. The dialysis device 7 is configured to capture the voltage values measured by the voltage metering units. Thus for example this can be by means of the transmission units 1013 shown in FIG. 1, which can be, as described above, contacts, coils or other means. Using the voltage values measured by the voltage metering units, the dialysis device 7 determines, according to the present example embodiment, the corresponding voltage value for each channel 1011, 1012. If a plurality of voltage values were measured by a plurality of voltage metering units for one channel 1011, 1012, calculations of average values can for example be used for this. Such calculations to determine a general, representative voltage value from a plurality of measured voltage values are familiar to the skilled person, and hence such calculations will not be discussed in greater detail here.

According to the present example embodiment, the dialysis device 7 uses the voltage value determined for the first channel 1011 and the voltage value determined for the second channel 1012 to calculate a difference between the voltages or voltage values of the two channels 1011, 1012. As already explained, this difference corresponds to the ultrafiltration rate.

According to the present example embodiment, the dialysis device 7 has a control or regulating unit 72, which is configured to control or regulate the flow of at least one of the blood or the dialysis streams 105, 106, by means of the calculated difference between the voltages of the first and the second channel 1011, 1012 of the sensor 101. The control or regulating unit 72 can control or regulate the flow, for example by a suitable adjustment of the blood pump and/or the dialysate pump, when the control or regulating unit 72 has received the present difference between the voltages and, after evaluation of the difference, has determined that the difference does not correspond to the ultrafiltration rate that was prescribed by the physician. The control or regulating unit 72 carries out the control or regulation of at least one of the blood or the dialysis streams 105, 106 in such a manner that after the control or regulation by the control or regulating unit 72 the current ultrafiltration rate or difference between the voltages in the channels 1011, 1012 corresponds to the prescribed ultrafiltration rate or difference between the voltages in the channels 1011, 1012, which can be achieved for example by a suitable adjustment of the blood pump and/or the dialysate pump.

According to the present example embodiment, after the calculation of the difference between the current voltages in the channels 1011, 1012 or the current ultrafiltration rate, the dialysis device 7 is configured to transmit to the control or regulating unit 72 a signal 73 which contains the difference between the current voltages in the channels 1011, 1012 or the current ultrafiltration rate. If the difference between the present voltages in the channels 1011, 1012 or the present ultrafiltration rate does not correspond to the difference between the present voltages in the channels 1011, 1012 or the ultrafiltration rate, that was prescribed by the physician, the control or regulating unit 72 controls or regulates the blood or the dialysis streams 105, 106 as described above.

Thus the present invention relates to the balancing of fluid streams in a dialysis system. In particular the invention relates to a cassette for conveying a first and a second fluid stream in a dialysis system, wherein the first and the second fluid streams can be medical fluid streams such as for example dialysate streams or blood streams, wherein the cassette has a sensor as a device for balancing the first and the second fluid stream, and wherein the sensor has a first channel for the first fluid stream and a second channel for the second fluid stream. The invention further relates to a dialysis system, which is configured to accommodate at least one cassette which is configured as described above. Furthermore, the present invention relates to an arrangement by which two channels for the first and the second fluid streams are formed. In addition, the invention relates to a method for construction of the two channels or the arrangement.

Although the invention is explained above with reference to the example embodiments according to the drawings attached, it is evident that the invention is not limited to these, but can instead be modified within the scope of the inventive idea which is disclosed above and in the pending claims. It is self-evident that there can be other additional example embodiments which represent the principle of the invention and are equivalent, and that therefore various modifications can be implemented without deviation from the scope of the invention. Thus for example the channels of the sensors or the fluid passageways of the parts for constructing an arrangement with two channels can have various forms, or various methods of calculation can be used for determining a representative voltage value for a channel by means of various voltages or voltage values measured for the channel.

LIST OF REFERENCE SIGNS

10 cassette
11 dialysis filter
101 sensor
102 inlet
103 outlet
104 dialysate pump
105 fluid stream
106 fluid stream
107 centering unit
108 ultrafiltration pump 1011 channel in sensor
1012 channel in sensor
1013 transmission units
20 orientation of the magnetic field to be used
21 measuring cell of the sensor
31 voltage metering units as electrodes
32 voltage metering units as electrodes
40 dividing wall
41 blood stream, fluid stream or dialysate stream
42 blood stream, fluid stream or dialysate stream
411 voltage metering unit as electrode
421 voltage metering unit as electrode
43 voltage metering unit as electrode
50 fluid passageway
51 first (component) part
52 second (component) part
53 third (component) part
54_1 channel
54_2 channel
55 voltage metering unit as electrode
56 nubs as fastening devices
57 recesses as fastening devices
60 fluid passageway
61 first (component) part
62 second (component) part
63 third (component) part
64_1 channel
64_2 channel
66 nubs as fastening devices
67 recesses as fastening devices
7 dialysis device
71 accommodation means, accommodation unit
72 regulating or control unit
73 signal

The invention claimed is:

1. A method for controlling/regulating an ultrafiltration rate in a dialysis device, wherein the dialysis device has a dialysis filter with a blood side and dialysate side separated by a semipermeable membrane, which method comprises:
providing the dialysis device with a single dialysate pump arranged upstream of the dialysis filter
causing blood to flow through the blood side of the dialysis filter in an extracorporeal blood circuit by a blood pump;
causing dialysate to flow through the dialysate side of the dialysis filter by the single dialysate pump;
determining a difference between dialysate flow rate into the dialysis device and dialysate flow rate out of the dialysis device using at least one sensor measuring the dialysate flow rate into the dialysis device and the dialysate flow rate out of the dialysis device; and
controlling/regulating an ultrafiltration rate of the dialysis device by a controlling and regulating unit, by adjusting a delivery rate of the blood pump and/or dialysate pump using a sensor signal from the at least one sensor.

2. The method according to claim 1, wherein the adjustment of the delivery rate is dependent on an actual value of the difference between dialysate flow rates into and out of the dialysis device, respectively, determined by the at least one sensor, and wherein the delivery rate is adapted if the actual value deviates from a provided predefined ultrafiltration rate and/or a provided predefined ultrafiltration volume.

3. The method according to claim 1, wherein the dialysate is delivered by a dialysate pump arranged upstream from the dialysis filter.

4. The method according to claim 1, wherein the controlling or regulating unit for adjusting a delivery rate is dependent on an actual value of the difference flow determined by the at least one sensor.

5. The method according to claim 1, wherein the controlling or regulating unit is configured to adapt the delivery rate when a determined difference value deviates from a provided predefined ultrafiltration rate and/or a provided predefined ultrafiltration volume.

6. The method according to claim 4, wherein the controlling or regulating unit is configured to adapt the delivery rate when a determined difference value deviates from a provided predefined ultrafiltration rate and/or a provided predefined ultrafiltration volume.

7. The method according to claim 1, wherein the at least one sensor has a first channel for the inflowing dialysate and a second channel for the outflowing dialysate, wherein the first channel and the second channel are oriented parallel to each other in a longitudinal direction and/or are oriented in such a way that the inflowing dialysate in the first channel and the outflowing dialysate in the second channel flow in opposite directions.

8. The method according to claim 6, wherein the at least one sensor has a first channel for the inflowing dialysate and a second channel for the outflowing dialysate, wherein the first channel and the second channel are oriented parallel to each other in a longitudinal direction and/or are oriented in such a way that the inflowing dialysate in the first channel and the outflowing dialysate in the second channel flow in opposite directions.

9. The method according to claim 7, wherein the first channel and the second channel are oriented substantially parallel to each other, and wherein the at least one sensor is configured to determine the difference between dialysate flowing into the dialysis device and dialysate flowing out of the dialysis device by exposing the first channel and the second channel to a magnetic field, wherein the magnetic field is directed substantially perpendicular to the first channel and to the second channel.

10. The method according to claim 9, wherein
the magnetic field causes a separation of positive and negative charge carriers in the inflowing dialysate of the first channel and in the outflowing dialysate of the second channel; and
the at least one sensor is configured to measure a first voltage, which is generated by the separation of positive and negative charge carriers in the inflowing dialysate and is provided through the flow of the inflowing dialysate in the first channel, and to measure a second voltage, which is generated by the separation of positive and negative charge carriers in the outflowing dialysate and is provided through the flow of the outflowing dialysate in the second channel, wherein the first and the second voltage are used to determine the difference between the inflowing dialysate and the outflowing dialysate.

11. The method according to claim 10, wherein the at least one sensor is configured to transmit at least one signal to the controlling and regulating unit of the dialysis device, said signal having the measured first and the measured second voltage or a value derived from the first and second measured voltage.

12. The method according to claim 10, wherein
at least one voltage measurement unit of the first channel is mounted on the first channel and is configured to measure the first voltage;
at least one voltage measurement unit of the second channel is mounted on the second channel and is configured to measure the second voltage;

the first channel has a voltage measurement unit of the first channel configured to measure a voltage generated by the separation in the inflowing dialysate, which voltage is provided through flow of the inflowing dialysate;

the at least one voltage measurement unit of the first channel is placed on a side of the first channel lying opposite a further side of the first channel on which the further voltage measurement unit of the first channel is placed, wherein the magnetic field is directed parallel to the one and to the further side of the first channel;

the second channel has a further voltage measurement unit of the second channel configured to measure a voltage generated by the separation in the outflowing dialysate, which voltage is provided through flow of the outflowing dialysate; and the at least one voltage measurement unit of the second channel is placed on a side of the second channel lying opposite a further side of the second channel on which the further voltage measurement unit of the first channel is placed, wherein the magnetic field is directed parallel to the one and to the further side of the second channel.

13. The method according to claim 11, wherein at least one voltage measurement unit of the first channel is mounted on the first channel and is configured to measure the first voltage;

at least one voltage measurement unit of the second channel is mounted on the second channel and is configured to measure the second voltage;

the first channel has a voltage measurement unit of the first channel configured to measure a voltage generated by the separation in the inflowing dialysate, which voltage is provided through flow of the inflowing dialysate;

the at least one voltage measurement unit of the first channel is placed on a side of the first channel lying opposite a further side of the first channel on which the further voltage measurement unit of the first channel is placed, wherein the magnetic field is directed parallel to the one and to the further side of the first channel;

the second channel has a further voltage measurement unit of the second channel configured to measure a voltage generated by the separation in the outflowing dialysate, which voltage is provided through flow of the outflowing dialysate; and the at least one voltage measurement unit of the second channel is placed on a side of the second channel lying opposite a further side of the second channel on which the further voltage measurement unit of the first channel is placed, wherein the magnetic held is directed parallel to the one and to the further side of the second channel.

14. The method according to claim 7, wherein the first channel and the second channel are formed from at least three parts of identical shape and size;

a liquid course is formed on at least one of two mutually opposite surfaces in each of the at least three parts; and the at least three parts for forming the first channel and the second channel are assembled by lining up the at least three parts on the sides of the at least three parts formed with liquid runs in such a way that the first channel is obtained between a first part and a second part of the at least three parts and the second channel is obtained between the second part and a third part of the at least three parts, wherein the first channel and the second channel have the same shape, are parallel to each other and are arranged alongside each other or one above the other.

15. The method according to claim 12, wherein the first channel and the second channel are formed from at least three parts of identical shape and size;

a liquid course is formed on at least one of two mutually opposite surfaces in each of the at least three parts; and the at least three parts for forming the first channel and the second channel are assembled by lining up the at least three parts on the sides of the at least three parts formed with liquid runs in such a way that the first channel is obtained between a first part and a second part of the at least three parts and the second channel is obtained between the second part and a third part of the at least three parts, wherein the first channel and the second channel have the same shape, are parallel to each other and are arranged alongside each other or one above the other.

16. The method according to claim 1, wherein at least the dialysate pump and the at least one sensor are enclosed by a cassette configured as a disposable article.

17. The method according to claim 14, wherein at least the dialysate pump and the at least one sensor are enclosed by a cassette configured as a disposable article.

18. The method according to claim 16, wherein the dialysis device has a seat for the cassette, and wherein the cassette is received in the seat.

* * * * *